(12) United States Patent
Kim et al.

(10) Patent No.: US 10,231,760 B2
(45) Date of Patent: Mar. 19, 2019

(54) INSTRUMENT FOR BAND COUPLING BETWEEN SPINOUS PROCESSES

(71) Applicants: SOLCO BIOMEDICAL CO., LTD., Pyeongtaek-si (KR); Hyeun-Sung Kim, Daejeon (KR)

(72) Inventors: Hyeun-Sung Kim, Daejeon (KR); Hong-Won Yoon, Gunpo-si (KR)

(73) Assignees: Solco Biomedical Co., Ltd., Pyeongtaek-si, Gyeonggi-do (KR); Hyeun-Sung Kim, Daejeon (KR)

( * ) Notice: Subject to any disclaimer, the term of this patent is extended or adjusted under 35 U.S.C. 154(b) by 0 days.

(21) Appl. No.: 15/523,599

(22) PCT Filed: Nov. 24, 2015

(86) PCT No.: PCT/KR2015/012638
§ 371 (c)(1),
(2) Date: May 1, 2017

(87) PCT Pub. No.: WO2016/085228
PCT Pub. Date: Jun. 2, 2016

(65) Prior Publication Data
US 2017/0311992 A1 Nov. 2, 2017

(30) Foreign Application Priority Data
Nov. 25, 2014 (KR) .................. 10-2014-0164952

(51) Int. Cl.
*A61B 17/70* (2006.01)
*A61B 17/84* (2006.01)

(52) U.S. Cl.
CPC ...... *A61B 17/7067* (2013.01); *A61B 17/7053* (2013.01); *A61B 17/7062* (2013.01); *A61B 17/7068* (2013.01); *A61B 17/84* (2013.01)

(58) Field of Classification Search
CPC ............ A61B 17/7068; A61B 17/7053; A61B 17/7062; A61B 17/82; A61B 17/842; A61B 17/7067
(Continued)

(56) References Cited

U.S. PATENT DOCUMENTS

| 6,626,944 B1 * | 9/2003 | Taylor | A61B 17/7062 606/249 |
| 8,092,459 B2 * | 1/2012 | Malandain | A61B 17/025 606/86 A |

FOREIGN PATENT DOCUMENTS

| KR | 10-0620115 B1 | 9/2006 |
| KR | 10-0850323 B1 | 8/2008 |

(Continued)

OTHER PUBLICATIONS

PCT International Search Report and Written Opinion dated Apr. 8, 2016 from corresponding Application No. PCT/KR2015/012638.

*Primary Examiner* — Pedro Philogene
(74) *Attorney, Agent, or Firm* — Dilworth IP, LLC

(57) ABSTRACT

The present invention relates to an instrument for band coupling between spinous processes that comprises: a needle unit that is inserted through a cutaway insertion portion of a patient's abdomen and is discharged through a cutaway discharge portion of the abdomen while passing between a spinous process protruding from the spine and a neighboring spinous process; and a band unit that is detachably coupled to an end portion of the needle unit and has a predetermined level of tension, the band unit being disposed between the spinous process and the neighboring spinous process, outside the spinous process, and outside the neighboring spinous process to secure the spinous process and the neighboring spinous process together. Thanks to the relatively cheap and simple configuration, it is possible to effectively conduct a procedure irrespective of proficiency, (Continued)

acquire an optimal procedure result, and cope with various patients' body types. In addition, the instrument can be maintained to be firmly secured after a procedure and can allow a micro-motion, thereby providing a state similar to the original spine to a patient.

12 Claims, 4 Drawing Sheets

(58) Field of Classification Search
  USPC ................................. 606/246–279, 74, 103
  See application file for complete search history.

(56) References Cited

FOREIGN PATENT DOCUMENTS

| | | | | |
|---|---|---|---|---|
| KR | 100850323 | * | 8/2008 | ......... A61B 17/7067 |
| KR | 10-1004937 B1 | | 12/2010 | |
| KR | 10-1013094 B1 | | 2/2011 | |
| KR | 10-1333657 B1 | | 11/2013 | |
| WO | 00-74594 A1 | | 12/2000 | |
| WO | WO0074594 | * | 12/2000 | ......... A61B 17/7058 |

* cited by examiner

INSTRUMENT FOR BAND COUPLING BETWEEN SPINOUS PROCESSES

BACKGROUND OF THE INVENTION

Field of the Invention

The present invention relates to a band coupling device between spinous processes and, more particularly, to a band coupling device between spinous processes, which fixes adjacent spinous processes, but permits a minute movement upon an operation for treating a vertebral disease, such as a spinal canal stenosis or a degenerative disc disease.

Discussion of the Related Art

A spinal canal is a passage through which a vertebral nerve passes. Holes at the rear of respective vertebrae are connected up and down to form a tunnel, and nerves continue from the brain to an arm and a leg through the tunnel.

If such a passage through which the vertebral nerve passes is narrowed, a patient is exposed to a disease, such as a spinal canal stenosis in which the patient feels a severe pain because the nerve is pressed.

The most common disc disease may be said to be a degenerative spinal canal stenosis.

Such a degenerative spinal canal stenosis is generated because as a vertebra experiences an aging process, a disc (intervertebral disc) that has caused a degenerative change pops out at the front and presses a nerve, a ligamentum flavum that surrounds the nerve becomes thick and hard-set at the back and presses the nerve, a facet joint located at the back of a spinal canal is swollen, and a vertebral nerve is pressed by a bone (bony spur) abnormally grown by the friction of the vertebra.

Recently, in order to treat such a spinal canal stenosis, an implant inserted between adjacent spinous processes is used a lot.

In general, a vertebral implant is for the fusion of spinous processes of patients who suffer from a degenerative disc disease, a spondylolisthesis, an external injury and a tumor.

However, a conventional vertebral implant has problems in that a spinous process is damaged and the vertebral implant escapes between spinous processes because upper and lower spinous processes are not fused, but are separately moved and thus a vertebra moves for a long period of time.

Furthermore, there are problems in that a long operation time is taken and the time taken for a patient to recover after the operation is long because a ligament must be cut in the rear of the back and the vertebral implant must be inserted in order to insert the vertebral implant between the spinous processes.

Furthermore, there is a problem in that the vertebral implant is not coupled to the upper and lower spinous processes perfectly and stably because a wing portion coupled to the upper and lower spinous processes is not configured to be adjusted according to the thickness of the spinous process after the vertebral implant is inserted between the spinous processes.

Furthermore, such a vertebral implant had a problem in that it is difficult to perform a procedure because the angle or width of a spinous process and adjacent spinous process is various depending on the body type of a patient.

In particular, such conventional vertebral implants had problems in that a production cost according to a mold design is high and the vertebral implants are economically inefficient because they have a complicate structure.

Furthermore, the conventional vertebral implants had a problem in that a high skill is required upon a procedure because the vertebral implants are complicated in structure as described above.

PRIOR ART DOCUMENT

Patent Document

Korean Patent No. 10-1004937
Korean Patent No. 10-1333657

SUMMARY OF THE INVENTION

The present invention has been invented to improve such problems, and an object of the present invention is to provide a band coupling device between spinous processes, which enables a procedure to be efficiently performed regardless of a skill and can obtain optimal procedure results through a relatively cheap and simple configuration.

Furthermore, an object of the present invention is to provide a band coupling device between spinous processes, which can be handled in accordance with various body types of patients and can provide a patient with the same state as that of the original vertebra, by permitting a minute movement while maintaining a fast fixing state after a procedure.

In order to accomplish the objects, the present invention provides a band coupling device between spinous processes, including a needle unit which is inserted into the dorsal part of a patient through an incised insertion part and which is capable of being discharged through a discharge part incised in the dorsal part through a space between a spinous process and adjacent spinous process protruded from vertebrae; and a band unit which is detachably coupled to the end of the needle unit, which has a specific degree of tension, and which is disposed between the spinous process and the adjacent spinous process and in the outskirts of the spinous process and the outskirts of the adjacent spinous process and fixes the spinous process and the adjacent spinous process.

In this case, the band unit permits a specific degree of operation between the vertebra from which the spinous process has protruded and the vertebra from which the adjacent spinous process has protruded.

In this case, the insertion part and the discharge part are incised in a width corresponding to the diameter of the needle unit.

Furthermore, the needle unit includes a needle body bent in an arc shape and having a specific diameter, a peak part provided in one end of the needle body and pointed toward a front end, and a coupling assembly provided in the other end of the needle body and having the band unit detached from and attached to coupling assembly. The peak part is inserted into the insertion part and discharged to the discharge part.

Furthermore, the insertion part and the discharge part are incised in a width corresponding to the diameter of the needle body.

Furthermore, the coupling assembly includes a protrusion stepwise incised from the other end of the needle body, a protruded piece protruded at a specific height from the protrusion, and a hook piece extended from the end of the protruded piece and bent toward the one end of the needle body.

Furthermore, the band unit includes a main band having a first length and permitting elastic transform and an assistant band having a second length shorter than the first length, permitting elastic transform, and having one end coupled at a specific point of the main band. One end of the main band and the other end of the assistant band are detachably coupled to the end of the needle unit and fixe the spinous process and the adjacent spinous process.

Furthermore, the band unit further includes a first rack hole which penetrates the one end of the main band and a first trapping ring which is coupled to the edge of the first rack hole and maintains the state in which the end of the needle unit has been hung and fixed.

Furthermore, the band unit further includes a second rack hole which penetrates the other end of the assistant band and a second trapping ring which is coupled to the edge of the second rack hole and maintains the state in which the end of the needle unit has been hung and fixed.

Furthermore, the band unit further includes a clamp piece which surrounds and fixes the one end of the assistant band and a portion to which the main band has been coupled.

Furthermore, the other end of the assistant band is disposed in the outskirts of the spinous process. The one end of the main band is disposed in the outskirts of the adjacent spinous process. The other end of the main band is disposed through the space between the spinous process and the adjacent spinous process.

Furthermore, the band coupling device further includes a spacer which is coupled to the main band and disposed in the space between the spinous process and the adjacent spinous process and which fixes the other end of the assistant band and the one end of the main band.

Furthermore, the band coupling device further includes a spacer which is coupled to the band unit and disposed in the space between the spinous process and the adjacent spinous process and which fixes the band unit.

Effects of the Invention

According to the present invention having the configuration, the following advantages can be accomplished.

First, in the present invention, the band unit fixes a spinous process and an adjacent spinous process as if it surrounds the outskirts of the spinous process and the outskirts of the adjacent spinous process between the spinous process and the adjacent spinous process, and has a specific degree of tension. Accordingly, an action can be taken in accordance with various body types of patients, and a fast fixing state can be maintained and a minute movement can also be permitted after a procedure.

Furthermore, the present invention has an advantage in that a procedure can be performed with a minimal invasive surgery (MIS) because a procedure can be performed if the insertion part and discharge part of a degree corresponding to the diameter of the thin needle unit having a specific diameter are formed in the cut dorsal part of a patient.

Accordingly, if a minimal invasive surgery (MIS) is performed using the band coupling device between spinous processes according to an embodiment of the present invention, the width of an operation incision portion can be formed to a minimum. Accordingly, the pain of a patient can be significantly reduced because the time taken for recovery after an operation can be significantly reduced.

Furthermore, the present invention has a relatively cheap and simple configuration including the needle unit and the band unit. Accordingly, a procedure can be efficiently performed regardless of a skill and optimal procedure results can be obtained.

Accordingly, the present invention can provide a patient with the same state as that of the original vertebra.

BRIEF DESCRIPTION OF THE DRAWINGS

FIGS. 3 and 4 are perspective views showing the state in which a needle unit, that is, a principal part of the band coupling device between spinous processes according to an embodiment of the present invention, has been first inserted into the dorsal part of the patient.

FIG. 5 is a concept diagram showing the state in which a band unit has been inserted after the needle unit, that is, a principal part of the band coupling device between spinous processes according to an embodiment of the present invention, penetrated the dorsal part of the patient.

FIGS. 6 and 7 are perspective views showing the state in which one end of the main band and other end of the assistant band of the band unit, that is, a principal part of the band coupling device between spinous processes according to an embodiment of the present invention, have penetrated the dorsal part of the patient.

FIG. 8 is an enlarged and perspective view showing the peripheral portion of a clamp piece which fixes the main band and assistant band of the band unit, that is, a principal part of the band coupling device between spinous processes according to an embodiment of the present invention.

FIGS. 9 and 10 are perspective views showing the state in which the needle unit connected to the other end of the assistant band of the band unit again, that is, a principal part of the band coupling device between spinous processes according to an embodiment of the present invention, has been inserted into the dorsal part of the patient.

FIG. 11 is a perspective view showing the state in which the other end of the assistant band has been discharged at the same time when the needle unit, that is, a principal part of the band coupling device between spinous processes according to an embodiment of the present invention, is discharged from the dorsal part of the patient.

FIG. 12 is a perspective view showing the state in which the needle unit connected to one end of the main band of the band unit again, that is, a principal part of the band coupling device between spinous processes according to an embodiment of the present invention, has been inserted into the dorsal part of the patient.

FIG. 13 is a perspective view showing the state in which one end of the main band of the band unit, that is, a principal part of the band coupling device between spinous processes according to an embodiment of the present invention, has been discharged from the dorsal part of the patient and thus the three distal ends of the band unit have been generally exposed to the dorsal part of the patient.

FIG. 14 is a perspective view showing the state in which the three distal ends of the band unit, that is, a principal part of the band coupling device between spinous processes according to an embodiment of the present invention, have been further tightened based on a spinous process and an adjacent spinous process.

FIG. 15 is a perspective view showing the state in which a spacer is coupled to the main band of the band unit, that is, a principal part of the band coupling device between spinous processes according to an embodiment of the present invention.

DETAILED DESCRIPTION OF THE EMBODIMENTS

Figure 1:
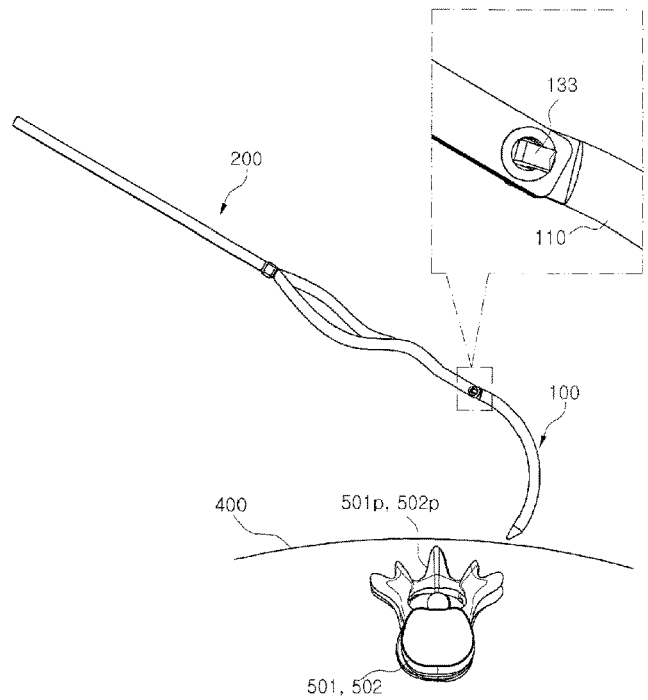
FIG. 1 is a perspective view showing an overall structure of a band coupling device between spinous processes according to an embodiment of the present invention.

The merits and characteristics of the present invention and methods for achieving the merits and characteristics will become evident from embodiments described in detail later in conjunction with the accompanying drawings.

However, the present invention is not limited to the disclosed embodiments, but may be implemented in various different ways.

In the specification, the embodiments are provided to only complete the disclosure of the present invention and to allow a person having ordinary skill in the art to which the present invention pertains to completely understand the category of the invention.

Furthermore, the present invention is only defined by the category of the claims.

Accordingly, in some embodiments, well-known elements, well-known operations, and well-known technologies are not described in detail in order to avoid the present invention from being ambiguously construed.

Furthermore, in the entire specification, the same reference numerals denote the same elements, and terms used (mentioned) in the specification are for describing the embodiments and are not intended to limit the present invention.

In the specification, the singular form, unless specially described otherwise in the context, may include the plural form. An element and operation described as being "comprise (or include)" do not exclude the existence or addition of one or more elements and operations.

Unless defined otherwise, all of terms (including technological and scientific terms) used in the specification will be used as meanings which can be understood by a person having ordinary skill in the art to which the present invention pertains in common.

Furthermore, terms that are generally used and defined in dictionaries should not be construed as having ideal or excessively formal meanings unless defined otherwise.

Hereinafter, preferred embodiments of the present invention are described with reference to the accompanying drawings.

First, FIG. 1 is a perspective view showing an overall structure of a band coupling device between spinous processes according to an embodiment of the present invention.

Figure 2:
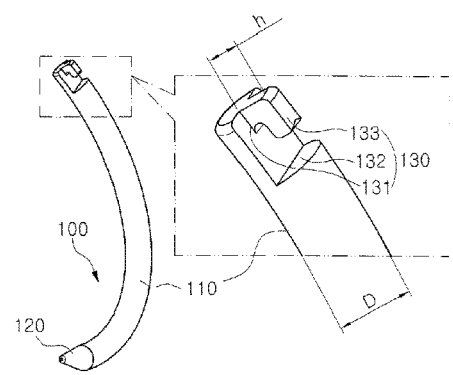
FIG. 2 is a perspective view showing an overall structure of a needle unit which is a principal part of the band coupling device between spinous processes according to an embodiment of the present invention.

Furthermore, FIG. 2 is a perspective view showing an overall structure of a needle unit which is a principal part of the band coupling device between spinous processes according to an embodiment of the present invention.

FIGS. 3 to 15 sequentially show a process of performing a procedure on a patient using the band coupling device between spinous processes according to an embodiment of the present invention.

It may be seen that the present invention has a structure including a needle unit (100) and a band unit (200), as shown.

The needle unit (100) may be inserted into the dorsal part (400) of a patient through an incised insertion part (401), may penetrate between a spinous process (501p) and adjacent spinous process (502p) protruded from a vertebra (501), and may be discharged through a discharge part (402) incised in the dorsal part (400). When a procedure is completed, the needle unit (100) is separated and eliminated from the body of the patient.

For reference, hereinafter, reference numeral 501p is used for a spinous process protruded from the vertebra (501). Such a spinous process is named a first spinous process 501p, for convenience sake.

Furthermore, reference numeral 502p is used for a spinous process adjacent to the first spinous process (501p). Such a spinous process is named a second spinous process (502p), for convenience sake, in order to distinguish it from the first spinous process (501p).

Furthermore, reference numeral 501 is used for a vertebra from which the first spinous process (501p) has protruded. Such a vertebra is named a first vertebra (501), for convenience sake.

Furthermore, reference numeral 502 is used for a vertebra from which the second spinous process (502p) has protruded. Such a vertebra is named a second vertebra (502), for convenience sake, in order to distinguish it from the first vertebra (501).

Meanwhile, the band unit (200) is detachably coupled to the end of the needle unit 100 and has a specific degree of tension. The band unit (200) is disposed between the first spinous process (501p) and the second spinous process (502p) and in the outskirts of the first spinous process (501p) and the outskirts of the second spinous process (502p), and fixes the first spinous process (501p) and the second spinous process (502p).

Accordingly, the present invention has a relatively cheap and simple configuration including the needle unit (100) and the band unit (200), and thus a procedure can be efficiently performed regardless of a skill and optimal procedure results can be obtained.

Furthermore, according to the present invention, the band unit (200) fixes the spinous process and the adjacent spinous process as if it surrounds the outskirts of the spinous process and the outskirts of the adjacent spinous process between the spinous process and the adjacent spinous process, and has a specific degree of tension. Accordingly, an action can be taken in accordance with various body types of patients, and a minute movement can be permitted while a fast fixing state is maintained after a procedure.

Accordingly, the present invention can provide a patient with the same state as that of the original vertebra.

The present invention may be applied to an embodiment, such as that described above, and may also be applied to the following various embodiments.

First, the insertion part (401) and the discharge part (402) are incised to the degree of a width corresponding to the diameter (D, hereinafter refer to FIG. 2) of the thin needle unit (100). Accordingly, a procedure can be performed on the band unit (200) with a minimal invasive surgery (MIS).

Furthermore, the band unit (200) has a specific degree of tension as described above. It is preferred that the band unit (200) is made of a material having excellent durability while generating elastic transform to permit a specific degree of operation between the first vertebra (501) from which the first spinous process (501p) has protruded and the second vertebra (502) from which the second spinous process (502p) has protruded.

That is, a material, such as medical polymer that is harmless to the human body and does not generate a rejection, may be used for the band unit (200).

Meanwhile, the structure of the needle unit (100) is described in detail with reference to FIG. 2. It may be seen that a peak part (120) and a coupling assembly (130) are provided at both ends of a needle body (110).

The needle body (110) is bent in an arc shape and has a specific diameter. If the needle body (110) is bent in an arc shape, the needle unit (100) can be inserted and discharged generally easily and the band unit (200) can be smoothly moved and guided.

The peak part (120) is provided at one end of the needle body (110) and is pointed toward the front end of the peak part. The peak part (120) enables the needle body (110) to be easily inserted through the insertion part (401).

The coupling assembly (130) is provided at the other end of the needle body (110), and the band unit (200) is attached to or detached from the coupling assembly (130).

Accordingly, the peak part (120) is inserted into the insertion part (401) and discharged from the discharge part (402). In a procedure process to be described later, the peak part (120) may be inserted through the discharge part (402) and discharged from the insertion part (401).

In this case, it is preferred that the insertion part (401) and the discharge part (402) are incised in a width corresponding to the diameter (D) of the needle body (110) in order to enable a minimal invasive surgery (MIS).

Accordingly, if a minimal invasive surgery (MIS) is performed using the band coupling device between spinous processes according to an embodiment of the present invention, the time taken for recovery after an operation can be significantly reduced because the width of an operation incision portion can be minimized.

Accordingly, the present invention can alleviate the pain of a patient.

Meanwhile, from the enlarged view of FIG. 2, it may be seen that the coupling assembly (130) has a protruded piece (132) and a hook piece (133) formed in a protrusion (131).

The protrusion (131) is formed by stepwise incising the other end of the needle body (110) and is formed by incising part of the other end of the needle body (110) having the specific diameter (D).

The protruded piece (132) is protruded at a specific height from the protrusion (131). The hook piece (133) is extended from the end of the protruded piece (132) and bent toward one end of the needle body (110).

Accordingly, the hook piece (133) of the coupling assembly (130) may be hung and fixed in such a manner that the end of the band unit (200) is attached and detached as shown in FIG. 1.

Furthermore, it is preferred that a height (h, hereinafter refer to FIG. 2) at which the protruded piece (132) and the hook piece (133) have protruded from the protrusion (131) is the same as or lower than that of the outer surface of the needle body (110).

The height (h) may be said to be technical means for coupling the band unit (200) and enabling the band unit (200) to be smoothly discharged along with the needle body (110) as the needle body (110) is inserted, penetrated, and discharged through the dorsal part (400) of the patient in a process for performing a procedure.

Meanwhile, referring to FIGS. 3 to 8, it may be seen that the band unit (200) has a structure including a main band (210) having a first length and permitting elastic transform and an assistant band (220) having a second length shorter than the first length, permitting elastic transform, and having one end coupled at a specific point of the main band (210).

Figure 10:
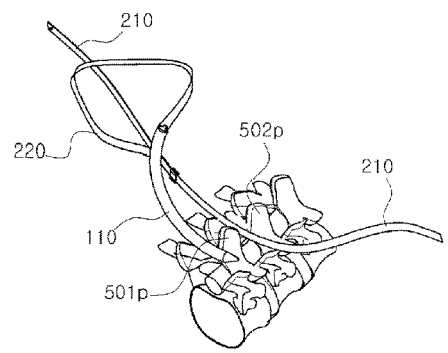

In this case, one end of the main band (210) and the other end of the assistant band (220) is hung on the end of the needle unit (100), that is, the hook piece (133) of the coupling assembly (130), and detachably coupled thereto, thereby fixing the first spinous process (501p) and the second spinous process (502p), refer to the state of FIG. 10.

Figure 6:
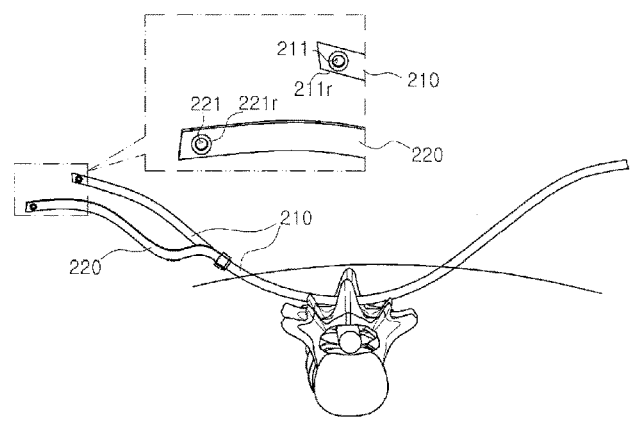

In this case, referring to FIG. 6, an embodiment, further including a first rack hole (211) which penetrates one end of the main band (210) and a first trapping ring (211r) which is coupled along the edge of the first rack hole (211) and maintains the state in which the end of the needle unit (100) has been hung and fixed, may be applied to the band unit (200).

Furthermore, referring to FIG. 6, an embodiment, further including a second rack hole (221) which penetrates the other end of the assistant band (220) and a second trapping ring (221r) which is coupled along the edge of the second rack hole (221) and maintains the state in which the end of the needle unit (100) has been hung and fixed, may be applied to the band unit (200).

The first and the second trapping rings (211r and 221r) are technical means for enabling one end of the main band (210) and the other end of the assistant band (220) to be smoothly moved according to the guidance of the needle unit (100) while maintaining the original shape and durability without being damaged or transformed in the process in which one end of the main band (210) and the other end of the assistant band (220) hung and fixed along with the hook piece (133) are repeatedly inserted, penetrate, and are discharged through the dorsal part (400) of the patient several times.

Figure 8:
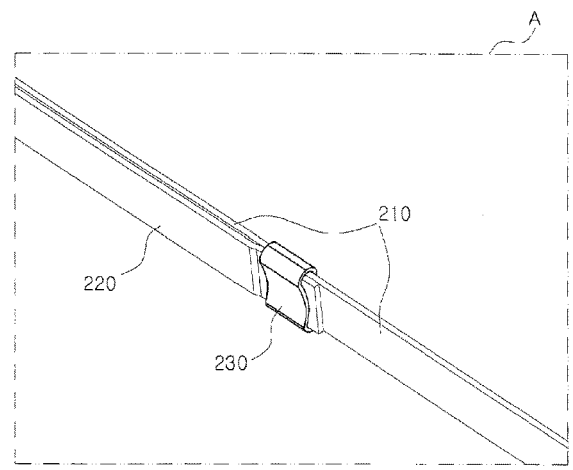

Furthermore, as shown in FIG. 8, it is preferred that the band unit (200) further includes a clamp piece (230) which surrounds and fixes one end of the assistant band (220) and a portion to which the main band (210) is coupled.

The clamp piece (230) is provided to maintain the state in which the band unit (200) has been concisely fixed and arranged by performing the role of a knot in the process in which the other end of the assistant band (220) is disposed in the outskirts of the first spinous process (501p), one end of the main band (210) is disposed in the outskirts of the second spinous process (502p), and the other end of the main band (210) is disposed through the space between the first spinous process (501p) and the second spinous process 502p when an operation is performed.

Meanwhile, the present invention may further include a spacer (300, hereinafter refers to FIG. 15) which is coupled to the main band (210) of the band unit (200) and disposed in the space between the first spinous process (501p) and the second spinous process (502p) and which fixes the other end of the assistant band (220) and one end of the main band (210) of the band unit (200).

The spacer (300) may be said to be provided to maintain the state in which the band unit (200) has been bound and fixed neatly and firmly while accurately maintaining the state in which the first and the second spinous processes (501p and 502p) have been spaced apart from each other at a specific interval.

A process for performing a procedure through the dorsal part (400) of a patient using the band coupling device between spinous processes according to an embodiment of the present invention is sequentially described with reference to FIGS. 3 to 15.

Figure 3:
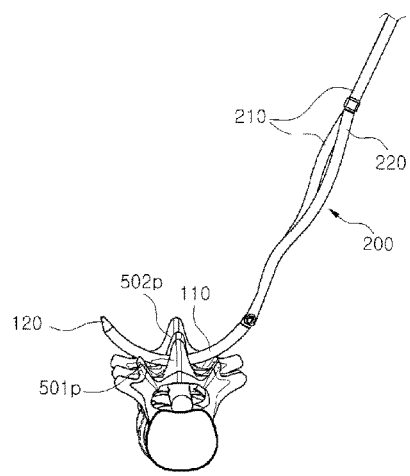
FIGS. 3 to 15 sequentially show a process of performing a procedure on a patient using the band coupling device between spinous processes according to an embodiment of the present invention.
Figure 4:
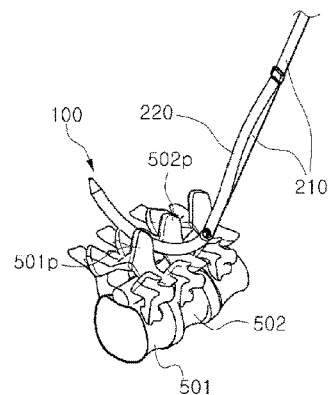

First, FIGS. 3 and 4 are perspective views showing the state in which the needle unit (100), that is, a principal part of the band coupling device between spinous processes according to an embodiment of the present invention, has been first inserted into the dorsal part (400) of the patient.

First, in order to perform a procedure with a minimal invasive surgery (MIS), a procedure person has incised and formed the insertion part (401) and the discharge part (402) on the left and right sides, respectively, based on the first and the second vertebrae (501 and 502) in a width approximately corresponding to the diameter (D) of the needle body (110) of the needle unit (100) in the dorsal part (400) of the patient.

Thereafter, the procedure person hangs and fixes one end of the main band (210) and the other end of the assistant band (220) on and to the hook piece (133) of the coupling assembly (130), grasps the needle body (110), and inserts it through the insertion part (401) from the peak part (120).

At this time, the peak part (120) needs to pass through the space between the first spinous process (501*p*) and the second spinous process (502*p*).

Figure 5:
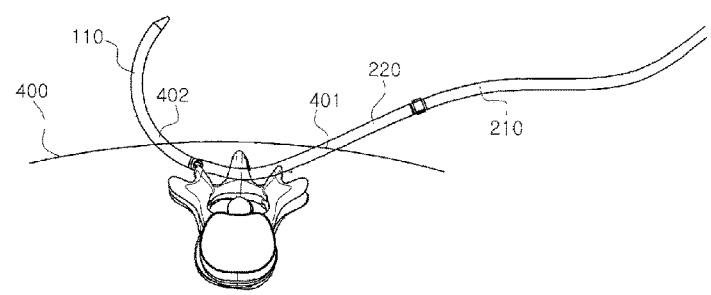

FIG. 5 is a concept diagram showing the state in which the band unit (200) has been inserted after the needle unit (100), that is, a principal part of the band coupling device between spinous processes according to an embodiment of the present invention, penetrated the dorsal part (400) of the patient.

In succession, when the procedure person inserts the needle body (110) so that the peak part (120) is discharged through the discharge part (402), one end of the main band (210) and the other end of the assistant band (220) pass through the space between the first spinous process (501*p*) and the second spinous process (502*p*), as shown.

Figure 7:
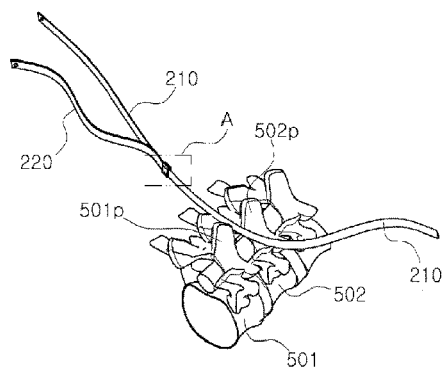

FIGS. 6 and 7 are perspective views showing the state in which one end of the main band (210) and other end of the assistant band (220) of the band unit (200), that is, a principal part of the band coupling device between spinous processes according to an embodiment of the present invention, have penetrated the dorsal part (400) of the patient.

Furthermore, FIG. 8 is an enlarged and perspective view showing the peripheral portion of the clamp piece (230) which fixes the main band (210) and assistant band (220) of the band unit (200), that is, a principal part of the band coupling device between spinous processes according to an embodiment of the present invention.

Next, when the procedure person pulls out the band unit (200) until the clamp piece (230) is discharged through the discharge part (402), the coupling between one end of the main band (210) and the other end of the assistant band (220), and the hook piece (130) of the needle unit (100) is released.

Figure 9:
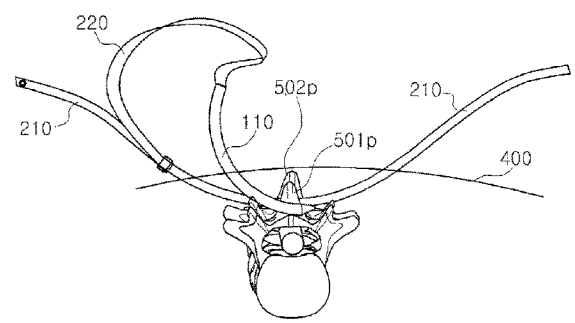

FIGS. 9 and 10 are perspective views showing the state in which the needle unit (100) connected to the other end of the assistant band (220) of the band unit (200) again, that is, a principal part of the band coupling device between spinous processes according to an embodiment of the present invention, has been inserted into the dorsal part (400) of the patient.

In succession, as shown, the procedure person hangs the hook piece (133) of the needle unit (100) on the other end of the assistant band (220) and inserts the peak part (120) from the discharge part (402).

At this time, the peak part (120) needs to pass through the outskirts of the first spinous process (501*p*).

Figure 11:
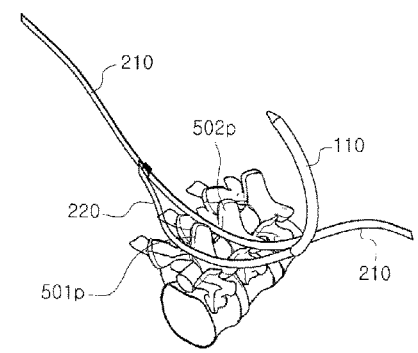

FIG. 11 is a perspective view showing the state in which the other end of the assistant band (220) has also been discharged at the same time when the needle unit (100), that is, a principal part of the band coupling device between spinous processes according to an embodiment of the present invention, is discharged from the dorsal part (400) of the patient.

Next, the procedure person draws the other end of the assistant band (220) out of the dorsal part (400) of the patient as far as possible by discharging the needle body (110) through the insertion part (401).

Thereafter, the procedure person releases the coupling between the hook piece 133 and the other end of the assistant band (220).

Figure 12:
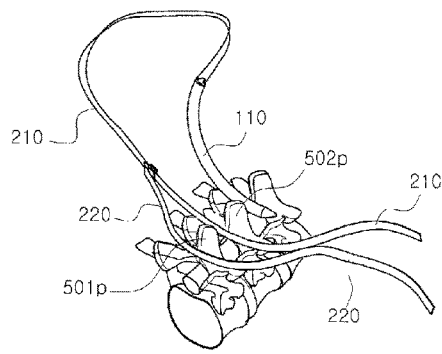

FIG. 12 is a perspective view showing the state in which the needle unit (100) connected to one end of the main band (210) of the band unit (200) again, that is, a principal part of the band coupling device between spinous processes according to an embodiment of the present invention, has been inserted into the dorsal part (400) of the patient.

In succession, the procedure person hangs the hook piece (133) of the needle unit (100) on one end of the main band (210) and inserts the peak part (120) from the discharge part (402), as shown.

At this time, the peak part (120) needs to pass through the outskirts of the second spinous process (502*p*).

Figure 13:
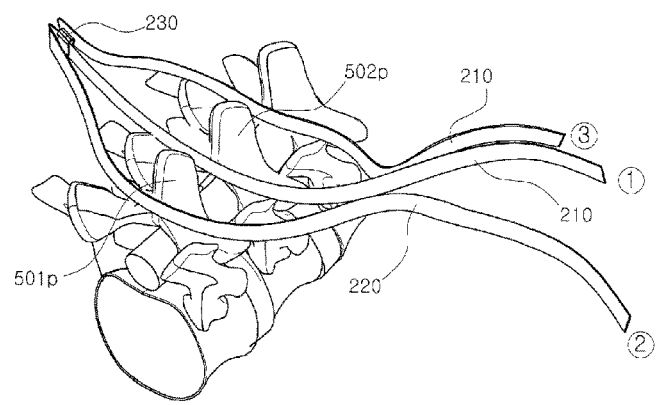

FIG. 13 is a perspective view showing the state in which one end of the main band (210) of the band unit (200), that is, a principal part of the band coupling device between spinous processes according to an embodiment of the present invention, has been discharged from the dorsal part (400) of the patient and thus the three distal ends (①, ②, and ③) of the band unit (200) have been generally exposed from the dorsal part (400) of the patient.

Next, the procedure person draws one end of the main band (210) out of the dorsal part (400) of the patient as far as possible by discharging the needle body (110) through the insertion part (401) as shown, and then releases the coupling between the hook piece (133) and one end of the main band (210).

Accordingly, the three distal ends (①, ②, and ③) of the band unit (200) have become the state in which they have been exposed from the dorsal part (400) of the patient.

Figure 14:
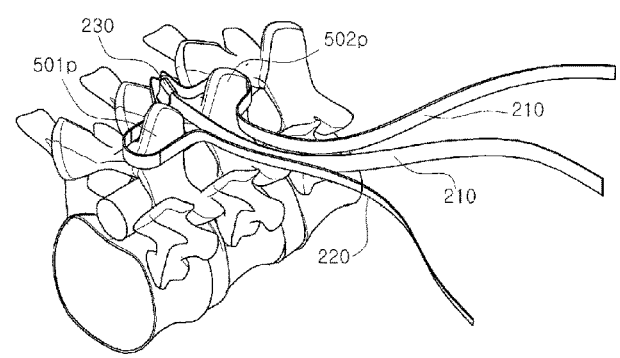

FIG. 14 is a perspective view showing the state in which the three distal ends (①, ②, and ③, hereinafter refer to FIG. 13) of the band unit (200), that is, a principal part of the band coupling device between spinous processes according to an embodiment of the present invention, have been further tightened based on the first spinous process (501*p*) and the second spinous process (502*p*).

Thereafter, the procedure person applies tension so that the state in which the three distal ends (①, ②, and ③) are tightened is maintained by pulling the three distal ends (①, ②, and ③), as shown.

Figure 15:
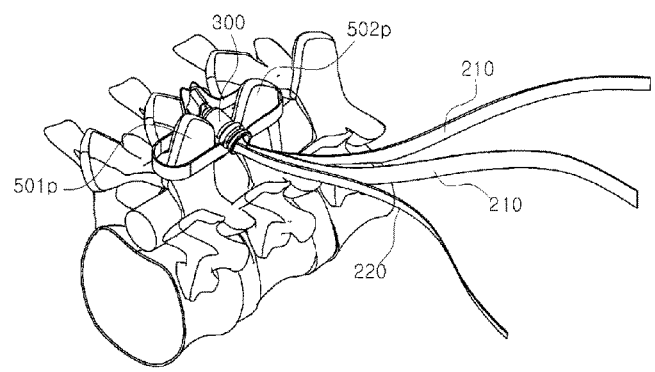

FIG. 15 is a perspective view showing the state in which the spacer (300) is coupled to the main band (210) of the band unit (200), that is, a principal part of the band coupling device between spinous processes according to an embodiment of the present invention.

In succession, as shown, the procedure person couples the spacer 300 from the distal end ② of the three distal ends (①, ②, and ③), that is, the other end of the main band (210), moves the spacer (300), inserts the spacer (300) through the insertion part (401), and disposes the spacer (300) between the first spinous process (501*p*) and the second spinous process (502*p*).

At this time, the remaining distal ends ① and ③ of the three distal ends (①, ②, and ③), that is, the other end of the assistant band (220) and one end of the main band (210), also pass through the spacer (300) and are fixed.

Thereafter, the procedure person cuts the three distal ends (①, ②, and ③) fixed to the spacer (300) in such a manner that they are closely attached to the spacer (300), and then seals the insertion part (401) and the discharge part (402), thereby completing the procedure.

As described above, it may be seen that the basic technical spirit of the present invention is to provide the band coupling device between spinous processes, wherein a procedure can be efficiently performed regardless of a skill, optimal procedure results can be obtained, an action can be taken in accordance with various body types of patients, and the same state as that of the original vertebra can be provided to a patient by permitting a minute movement while maintaining a fast fixing state after a procedure through a relatively cheap and simple configuration.

Furthermore, many other modifications and applications are also possible by a person having ordinary skill in the art without departing from the basic technical spirit of the present invention.

DESCRIPTION OF REFERENCE NUMERALS OF PRINCIPAL ELEMENTS IN THE DRAWINGS

100 . . . needle unit
110 . . . needle body
120 . . . peak part
130 . . . coupling assembly
131 . . . protrusion
132 . . . protruded piece
133 . . . hook piece
200 . . . band unit
210 . . . main band
211 . . . first rack hole
211r . . . first trapping ring
220 . . . assistant band
221 . . . second rack hole
221r . . . second trapping ring
230 . . . clamp piece
300 . . . spacer
400 . . . dorsal part
401 . . . insertion part
402 . . . discharge part
501 . . . first vertebra
502 . . . second vertebra (vertebra from which second spinous process 502p has protruded)
501p . . . first spinous process (spinous process)
502p . . . second spinous process (spinous process adjacent to spinous process).

What is claimed is:

1. A band coupling device between spinous processes, comprising:
   a needle which is inserted into a dorsal part of a patient through an incised insertion part and which is capable of being discharged through a discharge part incised in the dorsal part through a space between a spinous process and adjacent spinous process protruded from vertebrae; and
   a band which is detachably coupled to an end of the needle, which has a predetermined level of tension, and which is disposed between the spinous process and the adjacent spinous process and in outskirts of the spinous process and outskirts of the adjacent spinous process and fixes the spinous process and the adjacent spinous process
   wherein the band comprises:
   a main band having a first length and permitting elastic transform, and
   an assistant band having a second length shorter than the first length, permitting elastic transform, and having one end coupled at a point of the main band, and
   one end of the main band and the other end of the assistant band are detachably coupled to an end of the needle and fix the spinous process and the adjacent spinous process.

2. The band coupling device of claim 1, wherein the band permits operation between the vertebra from which the spinous process has protruded and the vertebra from which the adjacent spinous process has protruded.

3. The band coupling device of claim 1, wherein the insertion part and the discharge part are incised in a width corresponding to a diameter of the needle.

4. The band coupling device of claim 1, wherein:
   the needle comprises:
      a needle body bent in an arc shape,
      a peak part provided in one end of the needle body and pointed toward a front end, and
      a coupling device provided in the other end of the needle body and having the band detached from and attached to coupling device, and
      the peak part is inserted into the insertion part and discharged to the discharge part.

5. The band coupling device of claim 4, wherein the insertion part and the discharge part are incised in a width corresponding to a diameter of the needle body.

6. The band coupling device of claim 4, wherein the coupling device comprises:
   a protrusion stepwise incised from the other end of the needle body,
   a protruded piece protruded from the protrusion, and
   a hook piece extended from an end of the protruded piece and bent toward the one end of the needle body.

7. The band coupling device of claim 1, wherein the band further comprises:
   a first rack hole which penetrates the one end of the main band, and
   a first trapping ring which is coupled to an edge of the first rack hole and maintains a state in which the end of the needle has been hung and fixed.

8. The band coupling device of claim 1, wherein the band further comprises:
   a second rack hole which penetrates the other end of the assistant band, and
   a second trapping ring which is coupled to an edge of the second rack hole and maintains a state in which the end of the needle has been hung and fixed.

9. The band coupling device of claim 1, wherein the band further comprises a clamp piece which surrounds and fixes the one end of the assistant band and a portion to which the main band has been coupled.

10. The band coupling device of claim 1, wherein:
    the other end of the assistant band is disposed in the outskirts of the spinous process,
    the one end of the main band is disposed in the outskirts of the adjacent spinous process, and
    the other end of the main band is disposed through the space between the spinous process and the adjacent spinous process.

11. The band coupling device of claim 1, further comprising a spacer which is coupled to the main band and disposed in the space between the spinous process and the adjacent spinous process and which fixes the other end of the assistant band and the one end of the main band.

12. The band coupling device of claim 1, further comprising a spacer which is coupled to the band and disposed in the space between the spinous process and the adjacent spinous process and which fixes the band.

* * * * *